United States Patent [19]

Shearin

[11] Patent Number: 5,267,341
[45] Date of Patent: Nov. 30, 1993

[54] FLUID CATHETER WITH AQUEOUS FLUID CORE AND METHOD OF USE

[75] Inventor: Alan Shearin, El Toro, Calif.
[73] Assignee: Baxter International Inc., Deerfield, Ill.
[21] Appl. No.: 784,836
[22] Filed: Oct. 30, 1991
[51] Int. Cl.⁵ .............................................. G02B 6/00
[52] U.S. Cl. ........................................ 385/125; 128/3; 128/4; 606/15; 606/16
[58] Field of Search ..................... 128/3, 4, 6; 606/15, 606/16; 385/117, 118, 125

[56] References Cited

U.S. PATENT DOCUMENTS

| | | | |
|---|---|---|---|
| 3,995,934 | 12/1976 | Nath | 350/96 LM |
| 4,648,892 | 3/1987 | Kittrell et al. | 65/4.21 |
| 4,717,387 | 1/1988 | Inome et al. | 604/264 |
| 4,718,417 | 1/1988 | Kittrell et al. | 128/303.1 |
| 4,846,573 | 7/1989 | Taylor et al. | 385/118 |
| 4,927,231 | 5/1990 | Levatter | 385/125 |
| 4,985,029 | 1/1991 | Hoshino | 606/16 |
| 5,123,902 | 6/1992 | Müller et al. | 606/4 |

FOREIGN PATENT DOCUMENTS

| | | |
|---|---|---|
| 0105706 | 4/1984 | European Pat. Off. |
| 0173266 | 3/1986 | European Pat. Off. |
| 0246127 | 12/1987 | European Pat. Off. |
| 0247746 | 12/1987 | European Pat. Off. |
| WO90/04363 | 5/1990 | PCT Int'l Appl. |

OTHER PUBLICATIONS

IEE Journal of Quantum Electronics, vol. 26, No. 12, New York, pp. 2289-2296, K. W. Gregory et al., "Liquid Core Light Guide for Laser Angioplasty" (Dec. 1990).
European Patents Report of EP 246,552 (May 1987).
European Patents Report (p. 33, Week 8943) of EP 338,166 (Dec. 1988).

Primary Examiner—Rodney B. Bovernick
Assistant Examiner—Stephen W. Barns
Attorney, Agent, or Firm—Kurt, MacLean - Poms, Smith, Lande & Rose

[57] ABSTRACT

A light transmitting catheter includes a tube having a proximal end and a distal end. The tube contains aqueous fluid an interior surface on the tube has an index of refraction less than the index of refraction of water. The proximal end is provided with an adapter for receiving light from a light source associated with the proximal end of the tube and with an adapter for accepting an aqueous fluid to be passed throughout a substantial length of the tube for transmitting light to the distal end of the tube.

13 Claims, 3 Drawing Sheets

FLUID CATHETER WITH AQUEOUS FLUID CORE AND METHOD OF USE

BACKGROUND OF THE INVENTION

1. Field of the Invention

The present invention relates to fluid catheters for transmitting light, and more particularly to fluid catheters having a low refractive index clad and aqueous fluid core.

2. Related Art

Fluid catheters for transmitting light such as laser light to a selected location for medical treatment are well known. Nath U.S. Pat. No. 3,995,934, shows a flexible light guide for transmission of visible and near infrared light, and of light from a Nd-YAG-laser. The light guide includes a tube formed from flexible plastic material and filled with a liquid sealed between the ends of the tube by a material having a high transparency for the radiation to be transmitted. The liquid has an index of refraction approximately 1/10 higher than that of the plastics material of the tube. However, because the plastics have a higher index of refraction than aqueous solutions, the light guide typically uses organic solutions. Additionally, the range of usable solutions is often limited by the type of light being transmitted through the catheter.

light transmitting fluid catheters such as fluid laser catheters are commonly used for such medical applications as ablation of lesions and the like. One common application is using laser light to dissolve thromboses or stenoses where the laser light is directed at the target to dissolve it. However, where light energy is also absorbed in the fluid through which the light passes, such as an organic based fluid in the light catheter or around the target, the laser must often be pulsed several times to avoid overheating the fluid or the catheter, or the fluid must be continually infused through the target region to prevent overheating. In some cases, the power, duration and/or frequency of light application must be varied or reduced to prevent overheating.

There is a need, therefore, for a light transmitting catheter having an aqueous core. There is also a need for light transmitting catheters that are more efficient, and therefore absorb less light energy, do not heat up as much and can accept more flexible operating parameters than previously allowed. There is also a need for a light transmitting catheter which can use an aqueous core for transmitting light and also for infusing liquid into the area of interest. There is also a need for a light transmitting catheter which can be positioned using a guide wire rather than an inflation balloon.

Liquid filled light transmitting catheters are beneficial because of their small size and their flexibility. The ability to use a liquid core light guide avoids having to use a fixed length glass fiber inside the catheter tube, thereby avoiding the decreased flexibility caused by the frictional contract between the glass fiber and the wall of the lumen in which the glass fiber is placed. Liquid core light transmitting catheters are also structurally simpler than catheters incorporating glass fiber light guides.

SUMMARY OF THE INVENTION

In accordance with the present invention, a light transmitting catheter is provided which uses an aqueous core and can provide clear solutions to an area to be illuminated and which absorbs less energy, produces less heating of the catheter and fluid, and allows use of more flexible operating parameters during the use of the light transmitting catheter. In accordance with the present invention, a light transmitting catheter includes a tube having an interior surface for containing an aqueous fluid wherein the interior surface has an index of refraction less than the index of refraction of water. The tube has a distal end which will be positioned near the area of interest. A proximal end of the catheter includes means for receiving light from a light source associated with the proximal end the tube and further includes means for accepting an aqueous fluid to be passed throughout a substantial length of the tube for transmitting the light to the distal end of the tube.

In operation, an aqueous solution is passed into the catheter tube to fill the catheter tube. The distal end of the tube is preferably open so that the aqueous solution can pass out the distal portion of the tube. Light is passed through the aqueous solution to illuminate an object of interest external to the distal portion of the tube.

In a preferred embodiment of the invention, the inside surface of the tube is formed from an amorphous fluoropolymer such as Dupont's Teflon AF which has an index of refraction less than that of water. The amorphous fluoropolymer may be applied as a coating on the interior surface of a catheter tube, or may be used to form the catheter tube itself. Alternatively, the inside surface of the tube or the catheter tube itself may be formed from silanes such as bis[3-(triethoxysilyl)-propyl]tetrasulfide or methyldiethoxysilane having indices of refraction of 1.074 and 1.3275, respectively.

It is therefore an object of the present invention to provide a light transmitting catheter having an aqueous core. Such a catheter results in less light energy absorption by the catheter or fluid, less heating of the fluid and more flexible operation in terms of selection of operating parameters such as light pulse amplitude, duration and frequency.

It is also an object of the present invention to provide a light transmitting catheter having an aqueous core for transmitting light and which can infuse fluid into the area to be illuminated, if necessary, or which can transmit light at static fluid flow.

It is a further object of the present invention to provide a light transmitting catheter capable of transmitting light through a fluid in the catheter at a higher energy than previously possible.

It is an additional object of the present invention to provide a light transmitting catheter which can be manipulated and positioned using a guide wire, and which does not require an inflation balloon.

These and other objects of the present invention will be shown and described in the drawings and the following specification.

DETAILED DESCRIPTION OF THE PREFERRED EMBODIMENTS

Figure 1:
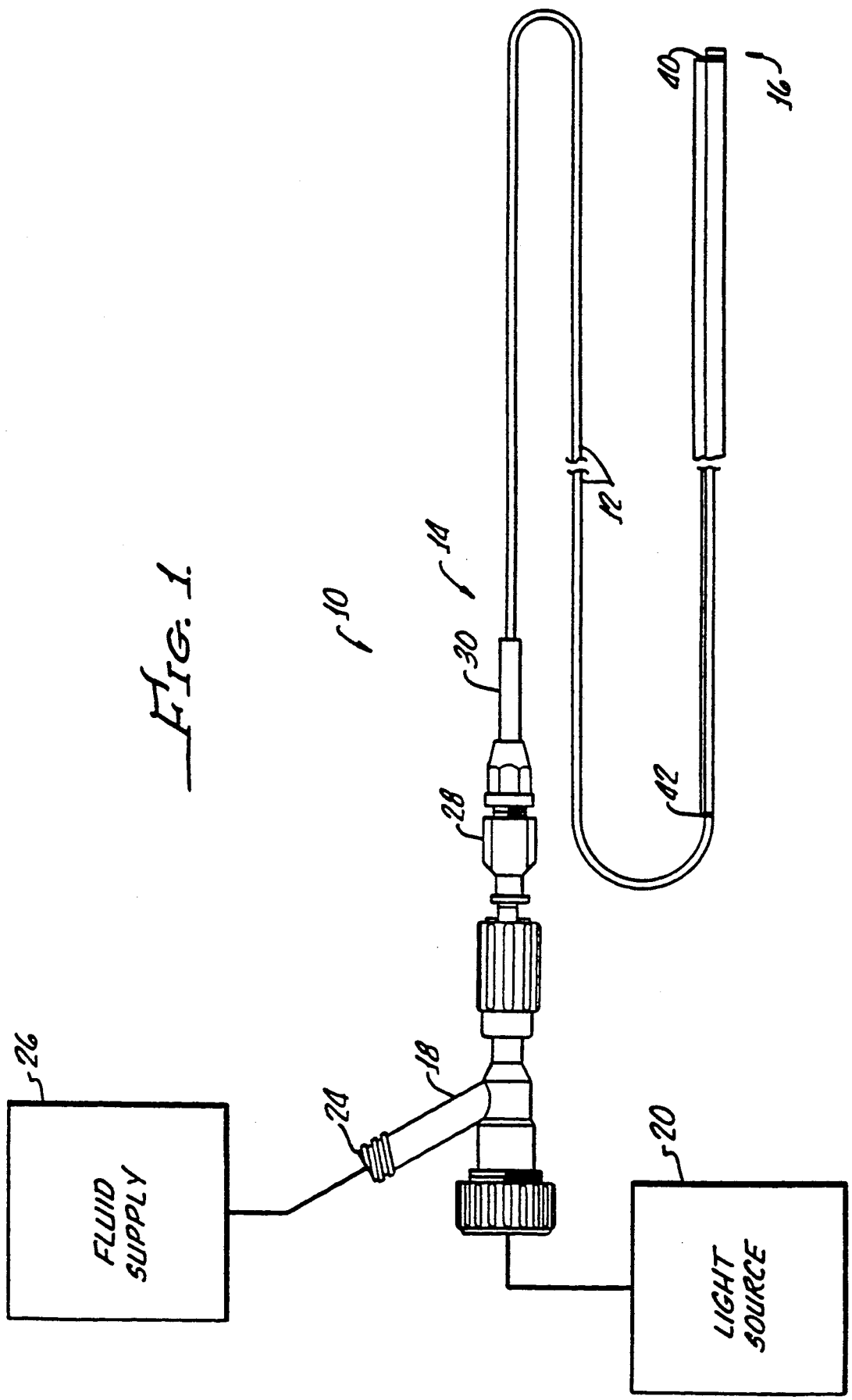
FIG. 1 is a side elevation view of a catheter according to the present invention showing a distal portion enlarged for detail.

In accordance with the present invention, a light transmitting catheter and a method for using the catheter provide improved treatment of biologic conditions since aqueous solutions can now be used as the catheter fluid and since energy absorption in the fluid is decreased, heating in the fluid is decreased and the treating physician has more flexibility in selecting operating parameters for treatment. A light transmitting catheter 10 includes a tube 12 having a proximal end 14 and an open distal end 16 (FIG. 1).

Various catheter components and equipment are associated with the proximal end, as is well known to those skilled in the art. The catheter includes a Y-connector 18 to which is coupled a light source 20 for providing light through the catheter tube 12 out the distal end 16 to illuminate an object of interest. The light source 20 preferably includes a fiber optic guide which passes into the catheter through an optical fiber port/lumen 22 and partway into the interior of the tube 12 to pass light from the light source through to the inside of the tube. An O-ring seal in the Y-connector seals the fiber optic guide in the catheter. The light source may be any suitable laser or other source such as a Nd-YAG-laser or a visible wave length laser operation between 400 and 700 nm.

The Y-connector further includes a fluid port 24 to which is coupled a fluid supply pump or reservoir 26. The fluid port 24 includes an appropriate channel for communicating fluid from the pump 26 to a primary lumen defined by the catheter tube 12. The Y-connector is coupled to a hub 28 and a strain relief 30, which components are well known to those skilled in the art.

Figure 2:
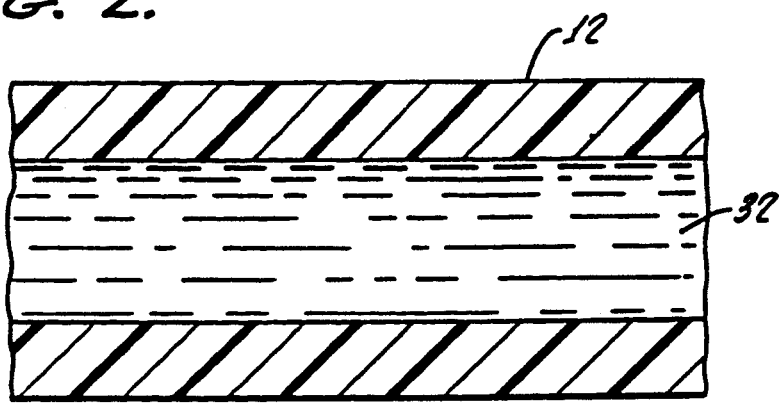
FIG. 2 is a segmental longitudinal cross section of a portion of the catheter body of FIG. 1 showing the catheter tube filled with fluid.
Figure 3:
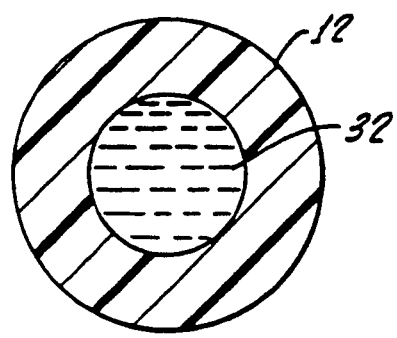
FIG. 3 is a traverse cross section of the catheter body of FIG. 1.

In a preferred embodiment, the catheter tube 12 is a single lumen plastic tube in fluid communication with the fluid port 24 so that aqueous solution from the fluid pump 26 can pass around the fiber optic from the light source 20 and fill the lumen in the catheter tube, and if necessary, pass out the distal end 16 to displace any fluid such as blood in the region of interest, for example around a thrombosis or stenosis. In one preferred embodiment (FIGS. 2 and 3), the plastic tube serves as a clad and the aqueous fluid 32 serves as a core to form an optic fiber combination for transmitting light from the light source to the region of interest. Specifically, light from the light source 20 (FIG. 1) passes from the fiber optic of the light source and into the fluid inside the catheter tube by internal reflection off of the inside surface of the clad, and out the distal end of the catheter tube 12 (FIG. 1).

The clad is preferably made from a polymer having an index of refraction less than 1.33, the index of refraction of water (based on the standard index of refraction at the sodium D line). Suitable polymers for practicing the present invention include amorphous fluoropolymer or silanes. Exemplary amorphous fluoropolymers include Dupont's Teflon (trademark) AF 1600 or 2400. The product Teflon AF 2400 has an optical transmission greater than 95% (ASTM method D 1003) and a refractive index of 1.29 (ASTM method D 542). Water absorption is less than 0.01% (ASTM method D570). Exemplary silanes include bis[3-(triethoxysilyl)propyl]-tetrasulfide, and methyldiethoxysilane. Both compounds are available from Petrarchsystems and have refractive indices of 1.074 and 1.3275, respectively.

The lower index of refraction of the clad material allows the use of aqueous solutions as the fluid core 32. The fluid can also be delivered to the location of interest for treatment, to flush the area or to serve as an environment replacing the blood while the thrombosis or other object is treated. As a result, a water-based fluid core will have a lower viscosity, making it easier to deliver fluid through the catheter and to the region of interest. Having a fluid with a lower viscosity also allows better contact with the clad and is more efficient for internal light reflection. An aqueous solution can be easily adjusted to account for scattering components and transmission, allowing the efficiency of the system to be controlled more closely than previously with organic solutions. Exemplary aqueous solutions having refractive indices in the 1.33 range include saline, Ringers lactate, heparin and numerous physiological fluids. The use of such fluids would allow fluid catheters to be used in a wide variety of applications. The catheter would not be limited to use of such fluids as glycerine, dextrose or even contrast media.

The low refractive index cladding and aqueous solution avoids having to vary the light parameters such as light energy, the pulse duration or the frequency of application of light energy to the region of interest in order to prevent overheating of the fluid, the clad or the treatment area. The light parameters used in previous application can be used in the present design. However, because liquids can be chosen having low energy absorption characteristics, the treating physician can vary the light source parameters to maximize the energy application to the area of interest without having to worry about excessive heating of the surrounding fluid. Where the light source is a laser light source, higher energy lasers can now be used without having to compensate for energy absorption in the fluid such as occurred with organic based fluids. The light absorption and diffusion problems resulting during use of organic fluids is minimized.

Using aqueous based solutions for the optical fiber core makes it easier to select a solution which is clear or less opaque than organic based solutions. As a result, energy transmission efficiency is increased, thereby reducing absorption and dispersion of light energy in the fluid. Using less opaque liquids allows use of higher energy light sources than previously possible, while still minimizing the likelihood of damaging the catheter. Efficiency is increased even using the energy levels, pulse lengths and energy levels used in prior applications.

Figure 4:
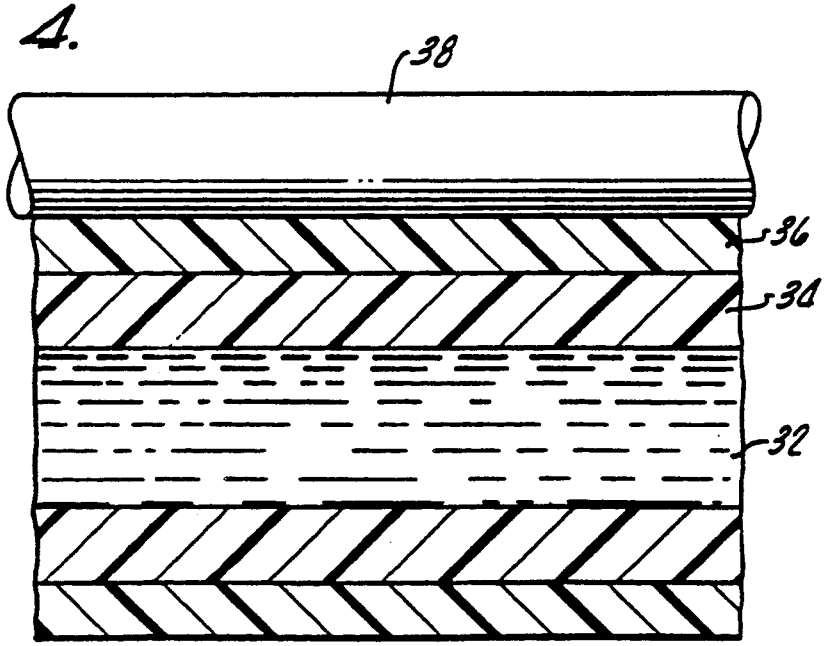
FIG. 4 is a segmental longitudinal cross section of a catheter body according to another aspect of the present invention and including a guide wire channel.

In an alternative embodiment of the invention (FIG. 4), the low refractive index clad 34, made preferably from the same material as the clad 12 of the catheter of FIG. 1, is formed on the inside of a catheter tube 36. The clad may be deposited or extruded or otherwise formed on the inside of a tube with a small thickness of around 1 angstrom but preferably ten to twenty microns thick. The catheter tube 36 may be formed from any suitable material to provide a reliable, flexible catheter tube having appropriate properties for transmitting light and minimizing the amount of heat which may build up in the catheter as a result of absorption.

In a further form of the invention, the catheter tube (12 in FIG. 1 or 36 in FIG. 4) includes a hollow guide wire channel 38 for accepting a suitable guide wire along at least a significant portion of the distal end of the catheter tube to assist in positioning and thereafter holding the catheter tube in place at the area of interest. The catheter tube and guide wire channel may be enclosed in and held together by a heat shrink tube placed over the length of the catheter tube. Suitable openings are formed in the heat shrunk tube to allow access by a guide wire. Alternatively, the guide wire channel may be bonded or otherwise adhered to the surface of the catheter tube as would be known to one skilled in the art.

One or more radiopaque markers may be formed on the distal portion of the catheter (FIG. 1). A first radiopaque marker 40 may be placed at the distal end 16 of the catheter tube while a second radiopaque marker 42 may be placed proximal of the first marker such as at the proximal end of the guide wire channel. Alternatively, the guide wire may be passed through a relatively short guide wire channel tip placed only along a small length at distal end 16 of the catheter tube so that the length of engagement of the guide wire with the guide wire channel is minimized.

The catheter tube 12 may be formed from an extrusion of the exemplary polymer such as amorphous fluoropolymer or silane. The amorphous fluoropolymer or silane may be extruded at a suitable rate, temperature and pressure on extrusion equipment designed for these materials.

Figure 5:
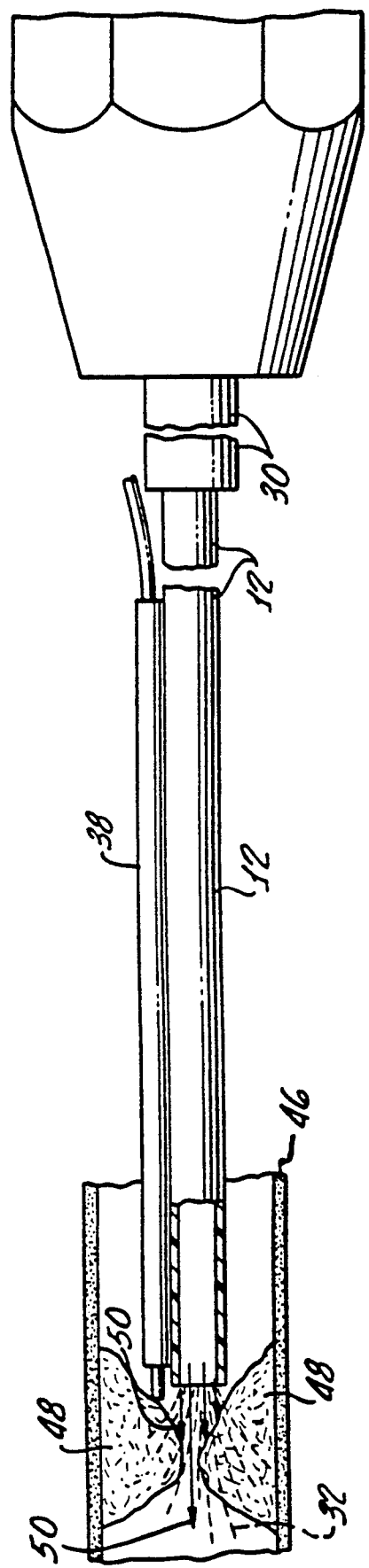
FIG. 5 is a segmented and partial longitudinal cross section of a catheter according to the present invention shown in the environment of a vessel having an object to be illuminated.

Consider now the method of use of the light transmitting catheter in conjunction with FIG. 5. The catheter, assembled with a suitable light source 20, such as a laser or other energy source and a fluid supply or pump 26 can be used to treat thrombosis, stenosis or other medical conditions. The core of the catheter body is filled with fluid and any air evacuated therefrom. A guide wire 44 is threaded onto the distal portion of the catheter through the guide wire channel and the combination introduced into the body region of interest. In the exemplary form shown in FIG. 5, the catheter is introduced into a vessel 46 having a thrombus 48 or other obstruction as the object of interest. The guide wire is used to assist in the positioning of and maintaining the catheter in place. When the catheter is properly positioned, light 50 is applied to the proximal end of the catheter and transmitted through the catheter core and out the distal end to be applied to dissolve or otherwise treat the object of interest after adjacent biological fluid has been flushed from the area by aqueous solution 32 from the catheter. While energy is being applied to the object of interest, fluid may be continually infused into the area to cool or flush the region. Alternatively, where energy absorption in the aqueous solution is minimal, the aqueous solution in the catheter may remain static. Energy may be applied to the area of interest according to standard energy profiles. Alternatively, where energy absorption or dispersion in the aqueous fluid is less than with previous organic solutions the light application profile may be changed accordingly. For example, the light energy may be increased, the duration extended or the frequency of the light pulses increased as appropriate.

With the open ended catheter described, any part of a vessel can be treated and any obstruction can be removed using an appropriate wavelength light source. If fluid is to be pumped through the catheter tube, the distal opening may be approximately 1 millimeter in diameter and a flow rate of approximately one third cc per second may be used for short interval pulses (on the order of ten seconds). Any conventional catheter injector may be used to supply the fluid to the catheter. However, it should be noted that it is not necessary to pump fluid through the catheter if the light transmission efficiency is relatively high. The ability to use relatively clear fluids allows a decrease in fluid flow without any concurrent decrease in application of energy to the area of interest. The fluid may even be static in some situations. The lower fluid flow results in less physiological risk resulting from application of external fluids.

The fluid used may be any aqueous combination of salts or pharmaceutical compounds such as thrombolytic drugs (for example, streptokinase, TPA urokinase and heparin solutions). Use of such compounds may result in an enhanced benefit when used in conjunction with the laser. Because of the increased efficiency in using aqueous and clear solutions, the guide wire can be used to position and maintain the catheter adjacent the area of interest, as opposed to using an inflatable balloon. The guide wire may also be passed through a separate lumen in the catheter.

The above are preferred configurations, but others are foreseeable. The described embodiments of the invention are only considered to be preferred and illustrative of the inventive concepts. The scope of the invention is not to be restricted to such embodiments. Various and numerous other arrangements may be devised by one skilled in the art without departing from the spirit and scope of the invention.

What is claimed:

1. A light transmitting catheter comprising:
   a tube having a proximal end, a distal end and an interior bore having a surface to contain an aqueous fluid, said surface having an index of refraction less than the index of refraction of water;
   an elongate optical fiber having a distal end and a proximal end, said optical fiber passing into the proximal end of said tube and extending partway through said tube bore, the proximal end of said fiber being connectable to a light source;
   an aqueous fluid inlet port for infusing aqueous fluid into said bore at a location proximal to the distal end of said optical fiber such that the aqueous fluid infused through said inlet port will flow around said optical fiber and fill the bore of said tube;
   whereby light transmitted through said optical fiber will pass from said optical fiber into the aqueous fluid inside the bore of said tube and be subsequently transmitted through said liquid to the distal end of said tube by total internal reflection.

2. The catheter of claim 1 wherein the tube includes a polymer having an index of refraction of less than 1.33 forming the interior surface.

3. The catheter of claim 2 wherein the tube is formed from the polymer.

4. The catheter of claim 2 wherein the tube is formed from a flexible plastic and includes an inside surface and the polymer is formed as a coating on the inside surface of the tube.

5. The catheter of claim 2 wherein said polymer is selected from the group consisting of amorphous fluoropolymer, bis[3-(triethoxysilyl)propyl]tetrasulfide, and methyldiethoxysilane.

6. The catheter of claim 1 wherein the tube distal end is open and aqueous solution from the catheter tube can be passed from the distal end of the tube.

7. The catheter of claim 1 further comprising a guide wire channel for accepting a guide wire for positioning the catheter.

8. The catheter of claim 7 further comprising a radiopaque marker on the distal end of the catheter tube.

9. A method of providing light to a distal location through a catheter, said method comprising the steps of:

provi ding an elongate catheter having a proximal end, a distal end and a bore extending longitudinally therethrough, said catheter bore having an inside tube surface having an index of refraction less than the index of refraction of water, a solid optical fiber being inserted into the proximal end of said catheter bore and extending partway therethrough;

infusing an aqueous liquid around said optical fiber such that said aqueous liquid fills said catheter bore;

passing light into the proximal end of said optical fiber, through said optical fiber, and into the aqueous liquid filling said catheter bore so that the light passes through said aqueous liquid and out the distal end of the tube by total internal reflection.

10. The method of claim 9 wherein the catheter tube is open at the distal end of the tube and wherein the step of passing light is carried out while the aqueous solution is static.

11. The method of claim 9 further comprising the step of passing aqueous solution through the tube while passing light through the aqueous solution.

12. The method of claim 11 wherein the step of passing the aqueous solution through the tube includes the step of passing a medicated aqueous solution through the catheter tube.

13. The method of claim 9 further comprising the step of positioning the catheter tube by positioning a guide wire while the guide wire is linked to the catheter.

* * * * *